United States Patent
Shioya et al.

(10) Patent No.: US 9,055,753 B2
(45) Date of Patent: *Jun. 16, 2015

(54) CONTAINER-PACKED BLACK COFFEE BEVERAGE

(75) Inventors: Yasushi Shioya, Sumida-ku (JP);
Yoshinobu Hayakawa, Sumida-ku (JP);
Shinji Yamamoto, Sumida-ku (JP);
Yoshikazu Ogura, Sumida-ku (JP)

(73) Assignee: Kao Corporation, Tokyo (JP)

( * ) Notice: Subject to any disclaimer, the term of this patent is extended or adjusted under 35 U.S.C. 154(b) by 1404 days.

This patent is subject to a terminal disclaimer.

(21) Appl. No.: 11/996,649

(22) PCT Filed: Jul. 28, 2006

(86) PCT No.: PCT/JP2006/315032
§ 371 (c)(1),
(2), (4) Date: Jan. 24, 2008

(87) PCT Pub. No.: WO2007/013615
PCT Pub. Date: Feb. 1, 2007

(65) Prior Publication Data
US 2010/0285182 A1  Nov. 11, 2010

(30) Foreign Application Priority Data
Jul. 29, 2005  (JP) ................ 2005-220884

(51) Int. Cl.
*A23F 5/18* (2006.01)
*A23F 5/24* (2006.01)
*A61K 36/74* (2006.01)

(52) U.S. Cl.
CPC ............. *A23F 5/243* (2013.01); *A23F 5/185* (2013.01); *A23V 2002/00* (2013.01); *A61K 36/74* (2013.01)

(58) Field of Classification Search
USPC ........................................................ 426/106
See application file for complete search history.

(56) References Cited

U.S. PATENT DOCUMENTS

| | | | | |
|---|---|---|---|---|
| 3,940,001 A | * | 2/1976 | Haefner et al. ............. | 215/12.2 |
| 5,178,896 A | * | 1/1993 | Langner ........................ | 426/590 |
| 5,438,109 A | * | 8/1995 | Nugent et al. ................ | 525/526 |
| 2003/0003212 A1 | * | 1/2003 | Chien et al. ................... | 426/548 |
| 2003/0144402 A1 | * | 7/2003 | Schenck ...................... | 524/445 |

FOREIGN PATENT DOCUMENTS

| | | |
|---|---|---|
| EP | 755631 A1 * | 1/1997 |
| EP | 1 716 757 A1 | 11/2006 |
| EP | 1 716 758 A1 | 11/2006 |
| EP | 1716757 A1 * | 11/2006 |
| GB | 1465168 A * | 2/1977 |
| JP | 57-28089 | 2/1982 |
| JP | 04-360647 | 12/1992 |
| JP | 5-111437 | 5/1993 |
| JP | 6-315434 | 11/1994 |
| JP | 07-313062 | 12/1995 |
| JP | 7-313063 | 12/1995 |
| JP | 2002-022062 | 1/2002 |
| JP | 2002-053464 | 2/2002 |
| JP | 2002-363075 | 12/2002 |
| JP | 2003-304812 | 10/2003 |
| JP | 2004-033023 | 2/2004 |
| JP | 2004-081207 | 3/2004 |
| JP | 2004-137287 | 5/2004 |
| JP | 2004-267158 | 9/2004 |
| JP | 2006-87306 | 4/2006 |
| JP | 2006-117631 | 5/2006 |
| JP | 2006-149235 | 6/2006 |
| JP | 2006-149236 | 6/2006 |
| JP | 2004-204191 | 8/2006 |
| JP | 2006-204192 | 8/2006 |
| JP | 3839831 B2 * | 11/2006 |
| WO | WO 2005/072533 A1 | 8/2005 |
| WO | WO 2005/072534 A1 | 8/2005 |

OTHER PUBLICATIONS

English abstract and English translation of the specification and claims of EP 755631 A1 from v3.espacenet.com.*
Identification of hydroxyhydroquinone in coffee as a generator of reactive oxygen species that break DNA single strands, Hiramoto et al., Tokyo Unifersity of Pharmacy and Life Science, 1432-1 Horinouchi, Hachioji, Tokyo 192-0392, Japan (1998).*
JP 3839831 B2, JPO machine translation (printed Sep. 20, 2013).*
U.S. Appl. No. 11/997,212, filed Jan. 29, 2008, Shioya, et al.
U.S. Appl. No. 11/997,219, filed Jan. 29, 2008, Hayakawa, et al.
U.S. Appl. No. 12/741,424, filed May 5, 2010, Ogura, et al.
M.L. Nurminen, et al., "Coffee, caffeine and blood pressure: a critical review", European Journal of Clinical Nutrition (1999), 53(11), pp. 831-839.
U.S. Appl. No. 13/878,087, filed Apr. 5, 2013, Yamamoto, et al.

* cited by examiner

*Primary Examiner* — Rena L Dye
*Assistant Examiner* — Chaim Smith
(74) *Attorney, Agent, or Firm* — Oblon, McClelland, Maier & Neustadt, L.L.P.

(57) ABSTRACT

Disclosed is a container-packed black coffee beverage which has an excellent hypertension ameliorating effect and can be ingested in an ordinary manner. A container-packed black coffee satisfying the following requirements (A) to (C): (A) a chlorogenic acid: 0.01 to 1% by mass; (B) hydroxyhydroquinone: 0.1% by mass or less relative to the mass of the chlorogenic acid; and (C) the chlorogenic acid/a coffee solid content ≥0.025 (by mass).

20 Claims, No Drawings

CONTAINER-PACKED BLACK COFFEE BEVERAGE

FIELD OF THE INVENTION

This invention relates to a packaged black coffee beverage that is suppressing hydroxyhydroquinone after the treatment of heat sterilization and has hypotensive effects.

BACKGROUND OF THE INVENTION

Examples of existing therapeutic agents for hypertension include a variety of neuroleptics acting on the regulation system associated with neural factors, ACE inhibitors acting on the regulation system related to liquid factors, AT acceptor antagonists, Ca antagonists related to the regulation system associated with substances derived from the vascular endothelial, and antihypertensive diuretics related to the hemoral modulation system in the kidneys. These therapeutic agents are used primarily for treating serious hypertensive patients at medical institutions. Under present circumstances, however, such medicines for hypertension are forcing the patients to bear heavy burdens due to adverse side effects thereof, though their effectiveness is satisfactory.

Meanwhile, an alimentary therapy, exercise therapy and general therapies for the improvements of lifestyle such as restrictions of drinking and smoking are widely employed for patients ranging from high normal blood-pressure patients, including mildly hypertensive patients, to severely hypertensive patients. As the importance of general therapies is increasingly acknowledged, the importance of improved dietary life continues to be talked about especially. There are a number of foods known as having hypotensive effects. Intensive searches for antihypertensive materials derived from food have conventionally been conducted, and many effective ingredients have been isolated and identified so far.

Among them, chlorogenic acids, caffeic acids, ferulic acids, which are contained in foods such as coffee, have been reported to show excellent hypotensive effects (Patent Documents 1 to 3). However, coffee beverages containing chlorogenic acids in large quantity are also reported to have no plainly recognizable hypotensive effects and tend to increase the blood pressure to the contrary (Non-patent Document 1).

[Patent Document 1] JP-A-2002-363075
[Patent Document 2] JP-A-2002-22062
[Patent Document 3] JP-A-2002-053464
[Non-patent Document 1] Eur. J. Clin. Nutr., 53(11), 831 (1999).

DISCLOSURE OF THE INVENTION

The present invention provides a packaged black coffee beverage satisfying the following conditions (A) to (C):
(A) from 0.01 to 1 wt % of chlorogenic acids,
(B) less than 0.1 wt % of hydroxyhydroquinone based on a content of the chlorogenic acids, and
(C) chlorogenic acids/solid content of coffee ≥0.025 (in terms of weight ratio).

DETAILED DESCRIPTION OF THE INVENTION

This invention relates to a packaged black coffee beverage, which has excellent hypertension-alleviating effects and can be ingested routinely.

The present inventors focused on the fact that coffee beverages do not show sufficient hypotensive effects despite their inclusion of chlorogenic acids, and thus conducted various investigations on whether there is any correlation between hypotensive effects and coffee beverage ingredients. As a result, it has been found that hydroxyhydroquinone contained in coffee beverages inhibits the hypotensive effects of chlorogenic acids. It has also been found that a coffee composition having excellent hypotensive effects can be obtained when the content of hydroxyhydroquinone is reduced to a specific level lower than its general content while maintaining the content of chlorogenic acids within a predetermined range.

However, it has been found that, when the coffee composition is formulated into a packaged beverage, hydroxyhydroquinone is reproduced during a heat sterilization process, even if the content of hydroxyhydroquinone is reduced beforehand. As a result of a further investigation, the additional formation of hydroxyhydroquinone by the heat sterilization process was successfully inhibited by controlling the proportion of chlorogenic acids in the solid content of coffee in a beverage at a specific level or higher.

The packaged black coffee beverage according to the present invention has excellent hypertension-alleviating effects, i.e., antihypertensive effects or blood-pressure-suppressing effects, and can be ingested over a long term. The packaged black coffee beverage according to the present invention is, therefore, useful as a medicine for the alleviation of hypertension or as a beverage labeled to the effect that it can be used for hypotension or for the suppression of an increase in blood pressure or labeled: "for those having higher blood pressure".

From the standpoints of hypotensive effects, blood-pressure-suppressing effects and taste, the packaged black coffee beverage according to the present invention contains from 0.01 to 1 wt %, preferably from 0.05 to 0.8 wt %, more preferably from 0.1 to 0.6 wt %, still more preferably from 0.13 to 0.5 wt %, even more preferably from 0.15 t 0.4 wt % of chlorogenic acids (A). As the chlorogenic acids (A), three chlorogenic acids, that is, ($A^1$) monocaffeoylquinic acid, ($A^2$) feruloylquinic acid and ($A^3$) dicaffeoylquinic acid are contained. As monocaffeoylquinic acid ($A^1$), one or more monocaffeoylquinic acids selected from 3-caffeoylquinic acid, 4-caffeoylquinic acid and 5-caffeoylquinic acid can be mentioned. As feruloylquinic acid ($A^2$), one or more feruloylquinic acid selected from 3-feruloylquinic acid, 4-feruloylquinic acid and 5-feruloylquinic acid can be mentioned. As dicaffeoylquinic acid ($A^3$), one or more dicaffeoylquinic acids selected from 3,4-dicaffeoylquinic acids, 3,5-dicaffeoylquinic acids and 4,5-dicaffeoylquinic acids can be mentioned. The content of such chlorogenic acids can be measured by high-performance liquid chromatography (HPLC). As a detection method in HPLC, UV detection is general, but detection at still higher sensitivity is also feasible by CL (chemical luminescence) detection, EC (electrochemical) detection, LC-Mass detection or the like.

In the packaged black coffee beverage according to the present invention, the weight percent ratio of hydroxyhydroquinone (B) to chlorogenic acid is less than 0.1, preferably from 0.001 to 0.07, more preferably from 0.002 to 0.05, still more preferably from 0.003 to 0.03, even more preferably from 0.004 to 0.02. When the weight percent ratio of hydroxyhydroquinone to chlorogenic acid is less than 0.1, the hypotensive effects of the chlorogenic acids can be fully exhibited. It is to be noted that the content of hydroxyhydroquinone in the beverage according to the present invention may be 0.

The content of such hydroxyhydroquinone can be measured by high-performance liquid chromatography (HPLC). As a detection method in HPLC, UV detection is general, but detection at still higher sensitivity is also feasible by CL (chemical luminescence) detection, EC (electrochemical) detection, LC-Mass detection or the like. EC (electrochemical) detection is particularly preferred in that it can measure even a very trace amount of hydroxyhydroquinone. It is to be noted that upon measurement of the content of hydroxyhydroquinone in a packaged black coffee beverage or the like by HPLC, the measurement may be conducted after its concentration.

Although the content of hydroxyhydroquinone can be directly measured by HPLC, hydroxyhydroquinone can also be quantitated by concentrating it from a packaged black coffee beverage or coffee composition in accordance with one of various chromatographic technologies and measuring the amount of the fraction of its concentrate.

It is to be noted that upon measurement of the content of chlorogenic acids, the measurement may preferably be conducted on a solution prepared by diluting the packaged black coffee beverage tenfold, for example, with a 5% acetonitrile solution, which contains 50 mM acetic acid, 10 mM sodium acetate and 0.1 mM 1-hydroxyethane-1,1-diphosphonic acid, or in a 4 to 5 (V/V) % acetonitrile solution system, which contains 40 to 50 mM acetic acid, 9 to 10 mM sodium acetate and 0.09 to 0.1 mM 1-hydroxyethane-1,1-diphosphonic acid, immediately after opening the packaged black coffee beverage. It is also to be noted that upon measurement of hydroxyhydroquinone, the measurement may preferably be conducted on a solution prepared by diluting the packaged black coffee beverage twofold with a 5 (V/V) % methanol solution, which contains 0.5 (W/V) % phosphoric acid and 0.5 mM 1-hydroxyethane-1,1-diphosphonic acid, or in a 2.5 to 5 (V/V) % methanol solution system, which contains 0.25 to 0.5 (W/V) % phosphoric acid and 0.25 to 0.5 mM 1-hydroxyethane-1,1-diphosphonic acid, immediately after opening the packaged black coffee beverage.

In the packaged black coffee beverage according to the present invention, the proportion of chlorogenic acids (CGA) (A) in the solid content of coffee in the beverage, that is, the weight ratio of chlorogenic acids/solid content of coffee is 0.025 or greater, preferably from 0.03 to 0.9, more preferably from 0.04 to 0.8, still more preferably from 0.04 to 0.6, even more preferably from 0.04 to 0.4, yet more preferably from 0.04 to 0.2. If this ratio is smaller than 0.025, the formation of hydroxyhydroquinone by heat sterilization processing cannot be inhibited sufficiently. It is to be noted that the chlorogenic acids is the total chlorogenic acid content (wt %) in the beverage or composition and is the total content of the three kinds of the respective chlorogenic acids ($A^1$) to ($A^3$), specifically the nine kinds of chlorogenic acids.

It is also to be noted that the term "solid content of coffee" does not mean the content of all solid components in the beverage or composition but is defined based on the following calculation formula and its unit is on a weight basis.

Solid content of coffee [wt %]=Brix degree–[sugars+dietary fibers]

wherein the respective terms are defined by the following calculation formulas:

Sugars=glucose+fructose+sucrose+maltose

As measurement methods of the individual terms, they are quantitated by the following methods.

Brix degree: Expressed by a degree (° Brix) indicated at 20° C. by a sugar refractometer.

It can be analyzed, for example, by "ATAGO RX-5000" (manufactured by ATAGO CO., LTD.). "Latest Soft Drinks" (published on Sep. 30, 2003 by KORIN PUBLISHING CO., LTD; described on page 243).

Sugars: glucose, fructose, sucrose, maltose;
high-performance chromatography (analyzed by Japan Food Research Laboratories).

Dietary fibers: High-performance chromatography (enzyme-HPLC method) (analyzed by Japan Food Research Laboratories).

It is to be noted that the term "dietary fibers" as used herein indicates the analysis targets by the analytical method described in "Standardized System for Food Nutrition Labeling", $2^{nd}$ Edition (published: Jul. 1, 1999, compiled: Japan Health Food & Nutrition Food Association, Nutrition Food Dept.; pages 46-51).

Further, the above-described analytical methods of the individual terms conform to the analytical methods described in "Merchandise Test Series" (12-5): Canned Coffees—How much sugar and caffeine are contained?—(published in November, 2001 by Consumers' Center of the Tokyo Metropolitan Government) and "Analytical Methods for Nutritional Components in Nutrition Labeling Standards", Notice of Apr. 26, 1999 (Notice No. 13) by the Director of Office of Health Policy for Newly Developed Foods, Life Sanitation Bureau, Ministry of Health and Welfare.

The packaged black coffee beverage according to the present invention may preferably contain general coffee components as they are, except for the reduction of the content of hydroxyhydroquinone.

In the packaged black coffee beverage according to the present invention, the content of $H_2O_2$ (hydrogen peroxide) may be preferably 1 ppm or lower, more preferably 0.1 ppm or lower, still more preferably 0.05 ppm or lower, even more preferably 0.01 ppm or lower from the standpoint of the inherent flavor and taste of coffee. The measurement of hydrogen peroxide can be conducted with any hydrogen peroxide meter employed in common. For example, "SUPER ORITECTOR MODEL 5" (high-sensitivity hydrogen peroxide meter manufactured by CENTRAL KAGAKU CORP.) or the like can be employed. $H_2O_2$ should be promptly analyzed immediately after opening the package in accordance with the measurement conditions described in U.S. Pat. Nos. 3,732,782 and 3,706,339, especially because $H_2O_2$ has been eliminated by sterilization processing before the opening of the package but, when exposed to air as a result of the opening of the package, $H_2O_2$ tends to gradually increase with time.

No particular limitation is imposed on the variety of coffee beans to be used for the packaged black coffee beverage according to the present invention, and Brazil, Columbia, Tanzania, Moca and the like can be mentioned as examples. As species of coffee, there are Arabic species and Robusta species. Single variety of coffee beans can be used, or plural varieties of coffee beans can be blended and used. No particular limitation is imposed on the roasting method for roasted coffee beans, and no limitations are imposed either on the roasting temperature and roasting atmosphere. Accordingly, an ordinary roasting method can be adopted. Moreover, no limitation is imposed either on the method of extraction from the beans. There can be mentioned, for example, a method that extracts coffee from roasted coffee beans or a grounded product thereof with water to hot water (0 to 100° C.) for from 10 seconds to 30 minutes. Extraction methods can include the boiling process, the espresso process, the siphon process, the drip process (paper, flannel or the like), etc.

The packaged black coffee beverage according to the present invention generally means one prepared by using coffee beans as much as 1 g or more, preferably 2.5 g or more, more preferably 5 g or more in terms of green beans per 100 g. The term "black coffee" as used herein means a coffee beverage which contains sugar, antioxidant and the like. Further, the packaged black coffee beverage may preferably be "single-strength". The term "single-strength" as used herein means a packaged beverage which is ready for drinking, as it is, without needing dilution after being opened.

The coffee composition useful for the packaged black coffee beverage according to the present invention can be obtained by treating an extract of roasted coffee beans with an adsorbent to lower the content of hydroxyhydroquinone such that the chlorogenic acids/solid content of coffee is controlled to 0.025 or higher. As the adsorbent, activated carbon, a reversed-phase chromatography medium or the like can be mentioned. More specifically, it can be only necessary to add an adsorbent to an extract of roasted coffee beans or an aqueous solution of a dry product of an extract of roasted coffee beans, to stir them at from 0 to 100° C. for from 10 minutes to 5 hours, and then to remove the adsorbed. The adsorbent may preferably used 0.02 to 1.0 times as much as the weight of roasted coffee beans in the case of activated carbon, or 2 to 100 times as much as the weight of roasted coffee beans in the case of a reversed-phase chromatography medium. For activated carbon, the average pore radius in the micropore range may be preferably 5 Angstroms (Å) or smaller, more preferably in a range of from 2 to 5 Angstroms, still more preferably in a range of from 3 to 5 Angstroms.

The term "micropore range" as used herein means 10 Angstroms and smaller, and as the average pore radius, the value of a pore radius corresponding to the peak top of a pore size distribution curve obtained by conducting a measurement by the MP method was employed. The MP method is the pore size measurement method described in a technical paper ("Colloid and Interface Science", 26, 46 (1968)), and is the method adopted by Sumika Chemical Analysis Service, Ltd. and Toray Research Center, Inc.

As the kind of activated carbon, palm shell activated carbon is preferred, with steam-activated palm shell activated carbon being more preferred. As commercial products of activated carbon, "SHIRASAGI WH2C" (Japan EnviroChemicals, Ltd.), "TAIKO CW" (Futamura Chemical Industries Co., Ltd.), "KURARAY COAL GW" (Kuraray Chemical Co., Ltd.) and the like can be used. As reversed-phase chromatography carriers, "YMS•ODS-A" (YMC Co., Ltd.), "C18" (GL Science, Inc.) and the like can be mentioned.

Among these adsorbent treatment methods, an adsorbent treatment method making use of specific activated carbon is preferred because it is not only capable of selectively lowering the content of hydroxyhydroquinone without reducing the content of chlorogenic acids but also industrially advantageous and moreover, it does not lower the content of potassium (retains at ⅕ or higher, specifically ½ or higher in weight ratio).

To control the chlorogenic acids/solid content of coffee in the coffee composition at 0.025 or greater in the present invention, the control can be effected by a method that controls the degree of roasts, the ratio of roasted beans to an extracting solution at the time of extraction, a method that separates into fractions an extract obtained at the time of extraction and draws only fractions which gives the intended chlorogenic acids/solid content of coffee, or a method that adsorb particular component (s) by activated carbon treatment. It is also possible to effect the control by further adding an extract from light roast beans or green beans.

The packaged black coffee beverage according to the present invention may preferably have no substantial peak in the time range of from 0.54 to 0.61 in terms of relative retention time to gallic acid when gallic acid is used as a standard substance in an analysis by high-performance liquid chromatography. For the confirmation of the existence of no substantial peal in the time range, general HPLC can be used. For example, this confirmation can be effected by using as an eluent a gradient eluent of a 0.05 M solution of acetic acid in water and a 0.05 M solution of acetic acid in 100% acetonitrile as an eluent and an ODS column and performing detection with an ultraviolet absorptiometer or the like.

The possession of no substantial peak by the relative retention time to gallic acid in the time range of from 0.54 to 0.61 in the present invention means S2/S1<0.01, in which S1 represents an area value obtained upon analysis of a 1 ppm solution of gallic acid and S2 represents the sum of peak areas ascribable to components eluted in the above-described specific range when the packaged black coffee beverage is analyzed under the same conditions.

To the packaged black coffee beverage according to the present invention, sugars such as sucrose, glucose, fructose, xylose, fructose-glucose solution and sugar alcohol, antioxidants, pH regulators, emulsifiers, flavors and the like can be added. The packaged black coffee beverage according to the present invention may preferably be a coffee beverage substantially free of milk components, i.e., so-called "black".

The pH of the packaged black coffee beverage according to the present invention may be preferably from 5 to 7, more preferably from 5.4 to 6.5, still more preferably from 5.6 to 6.3. As the ratio of constituents in monocaffeoylquinic acid in the packaged black coffee beverage, it is preferred the weight ratio of 4-caffeoylquinic acid/3-caffeoylquinic acid is from 0.6 to 1.2 and the weight ratio of 5-caffeoylquinic acid/3-caffeoylquinic acid is from 0.01 to 3. The packaged black coffee beverage according to the present invention can use a container such as a PET bottle, a can (aluminum or steel), a paper pack, a retort pouch or a bottle (glass). In this case, the container can have a capacity of from 50 to 2,500 mL. From the viewpoint of preventing changes in the components of coffee, a container of low oxygen permeability is preferred as the container. For example, the use of an aluminum or steel can, a glass bottle or the like is preferred. In the case of cans and bottles, recappable and resealable ones are also included. The term "oxygen permeability" means an oxygen permeability ($cc \cdot mm/m^2 \cdot day \cdot atm$) as measured under an environment of 20° C. and 50% relative humidity by an oxygen permeability meter for containers and films, and an oxygen permeability of 5 or lower can be preferred, with 3 or lower being more preferred, with 1 or lower being even more preferred.

Upon production of a packaged black coffee beverage, sterilization processing is generally conducted. When heat sterilization is feasible, the sterilization processing is conducted under the sterilization conditions prescribed in the Food Sanitation Act after being filled in a container such as a metal can. For those which cannot be subjected to retort sterilization like PET bottles or paper packs, a process is adopted such that the coffee beverage is sterilized beforehand at a high temperature for a short time under similar sterilization conditions as the conditions prescribed in the Food Sanitation Act, for example, by a plate-type heat exchanger, is cooled to a particular temperature, and is then filled in a package. It is also possible to conduct an operation such that subsequent to heat sterilization under aseptic conditions, the pH of the coffee beverage is caused to return to neutral under aseptic conditions or that subsequent to heat sterilization under neutral conditions, the pH of the beverage is caused to drop back to the acidic side under aseptic conditions.

The packaged black coffee beverage according to the present invention contains an effective amount of chlorogenic acids having hypertension alleviating effects and, even after heat sterilization processing, is lowered in the content of hydroxyhydroquinone which inhibits the hypertension alleviating effects of hydroxyhydroquinone. It is, therefore, useful as a hypotensive or blood-pressure-suppressing medicinal composition, a hypotensive beverage or a blood-pressure-suppressing beverage.

EXAMPLES

Analytical methods of chlorogenic acids and hydroxyhydroquinone are as follows:
Analytical Method of Chlorogenic Acids An analytical method of chlorogenic acids in a packaged black coffee beverage or coffee composition is as will be described hereinafter. HPLC was used as an analyzer. The followings are the model numbers of component units in the analyzer. UV-VIS detector: "L-2420" (Hitachi High-Technologies Corporation), column oven: "L-2300" (Hitachi High-Technologies Corporation), autosampler: "L-2200" (Hitachi High-Technologies Corporation), column: "CADENZA CD-C18", 4.6 mm inner diameter×150 mm length, particle size: 3 μm (Intact Corp.).

Analysis conditions are as follows. Sample injection volume: 10 μL, flow rate: 1.0 mL/min, wavelength preset for UV-VIS detector: 325 nm, preset column-oven temperature: 35° C., Eluent A: 5 (V/V) % acetonitrile solution containing 0.05 M of acetic acid, 0.1 mM 1-hydroxyethane-1,1-diphosphonic acid and 10 mM sodium acetate, Eluent B: acetonitrile.
Concentration Gradient Conditions

| Time | Eluent A | Eluent B |
|---|---|---|
| 0.0 min | 100% | 0% |
| 10.0 min | 100% | 0% |
| 15.0 min | 95% | 5% |
| 20.0 min | 95% | 5% |
| 22.0 min | 92% | 8% |
| 50.0 min | 92% | 8% |
| 52.0 min | 10% | 90% |
| 60.0 min | 10% | 90% |
| 60.1 min | 100% | 0% |
| 70.0 min | 100% | 0% |

In HPLC, a sample (1 g) was accurately weighed, its total volume was increased to 10 mL with Eluent A, and subsequent to filtration through a membrane filter ("GL CHROMATODISK 25A", pore size: 0.45 μm, GL Science, Inc.), the filtrate was provided for an analysis.
Retention Time of Chlorogenic Acids (Unit: min)

($A^1$) Monocaffeoylquinic acid: 3 kinds at 5.3, 8.8 and 11.6 in total, ($A^2$) feruloylquinic acid: 3 kinds at 13.0, 19.9 and 21.0 in total, and ($A^3$) dicaffeoylquinic acid: 3 kinds at 36.6, 37.4 and 44.2 in total. From the area values of the 9 kinds of chlorogenic acids as determined above, 5-caffeoylquinic acid was chosen as a standard substance, and its wt % was determined.
Analytical Method of Hydroxyhydroquinone by HPLC-Electrochemical Detector An analytical method of hydroxyhydroquinone in a packaged black coffee beverage or coffee composition is as will be described hereinafter. As an analyzer, an HPLC-electrochemical detector (the coulometric type) "COULARRAY SYSTEM" (model: 5600A, developed and manufactured by: ESA Analytical, Ltd., imported and sold by: MC MEDICAL, INC.), HPLC-electrochemical detector (the coulometric type), was used. The followings are the names and model numbers of component units in the analyzer.

Analytical cell: "MODEL 5010", coularray organizer, coularray·electronics module software: "MODEL 5600A", solvent feeder module: "MODEL 582", gradient mixer, autosampler: "MODEL 542", pulse damper, degasser: "DEGASYS ULTIMATE DU3003", column oven "505".
Column: "CAPCELL PAK C18 AQ", 4.6 mm inner diameter×250 mm length, particle size: 5 μm (Shiseido Co., Ltd.).

Analysis conditions are as follows.
Sample injection volume: 10 μL, flow rate: 1.0 mL/min, voltage applied to electrochemical detector: 0 mV, preset column-oven temperature: 40° C., Eluent A: 5 (V/V) % methanol solution containing 0.1 (W/V) % phosphoric acid, 0.1 mM 1-hydroxyethane-1,1-diphosphonic acid and 5 (V/V) % methanol solution, Eluent B: 50 (V/V) % methanol solution containing 0.1 (W/V) % phosphoric acid and 0.1 mM 1-hydroxyethane-1,1-diphosphonic acid.

For the preparation of Eluent A and Eluent B, distilled water for high-performance liquid chromatography (Kanto Chemical Co., Ltd.), methanol for high-performance liquid chromatography (Kanto Chemical Co., Ltd.), phosphoric acid (guaranteed reagent, Wako Pure Chemical Industries, Ltd.) and 1-hydroxyethane-1,1-diphosphonic acid (60% aqueous solution, Tokyo Kasei Kogyo Co., Ltd.) were used.
Concentration Gradient Conditions

| Time | Eluent A | Eluent B |
|---|---|---|
| 0.0 min | 100% | 0% |
| 10.0 min | 100% | 0% |
| 10.1 min | 0% | 100% |
| 20.0 min | 0% | 100% |
| 20.1 min | 100% | 0% |
| 50.0 min | 100% | 0% |

After a sample (5 g) was accurately weighed, its total volume was increased to 10 mL with a 5 (V/V) % methanol solution containing 0.5 (W/V) % phosphoric acid and 0.5 mM 1-hydroxyethane-1,1-diphosphonic acid. The solution was subjected to centrifugation to obtain an analysis sample of the supernatant. The supernatant was allowed to pass through "BOND ELUTE SCX" (packed weight of solid phase: 500 mg, reservoir capacity: 3 mL, GL Science, Inc.), and an initial volume (approx. 0.5 mL) of passed solution was diverted to obtain the passed solution. The passed solution was subjected to filtration through a membrane filter ("GL CHROMATODISK 25A", pore size: 0.45 μm, GL Science, Inc.), and the filtrate was promptly provided for its analysis.

In an analysis by the HPLC-electrochemical detector under the above-described conditions, the retention time of hydroxyhydroquinone was 6.38 minutes. From the area values of peaks obtained, their weight percentages were determined by using hydroxyhydroquinone (Wako Pure Chemical Industries, Ltd.) was a standard substance.

Example 1

Medium roast coffee beans were extracted with 8 volumes of deionized water (95° C.) to obtain a coffee extract. The Brix degree of the coffee extract was next measured, and a column (inner diameter: 45 mm, length: 150 mm) packed with activated carbon ("SHIRASAGI WH2C") in an amount as much as 50 wt % of the Brix degree was provided. Subsequently, the coffee extract was allowed to pass under the conditions of 25° C. and SV 8 [L/capacity [$m^3$]/flow rate [$m^3$/hr]] through the column packed with the activated carbon to subject the coffee extract to activated carbon treatment, and therefore, a coffee composition from which hydroxyhydroquinone had been removed was obtained.

The content of chlorogenic acids in the coffee composition obtained with hydroxyhydroquinone removed therefrom as described above was measured. The coffee composition was diluted with deionized water, and its pH was adjusted with sodium bicarbonate such that its pH value after heat sterilization processing became equal to the corresponding value shown in Table 1. Hydroxyhydroquinone before the heat sterilization was lower than its detection limit (the analytical method of hydroxyhydroquinone by HPLC-electrochemical detector). The coffee composition obtained as described above was filled in a 190-g can, sealed, and subjected to retort sterilization processing under the sterilization conditions shown in Table 1 to obtain a packaged black coffee beverage. For the hydroxyhydroquinone after the heat sterilization, the analytical method of hydroxyhydroquinone by HPLC-electrochemical detector was employed.

Examples 2-3

Packaged black coffee beverages were produced in a similar manner as in Example 1 except that the degree of roasts and SV were varied to control the chlorogenic acids/solid content of coffee, respectively.

Comparative Example 1

Through a column (inner diameter: 45 mm, length: 150 mm) packed with activated carbon ("MOLSIEVON X2M") in an amount as much as 50 wt % of the Brix degree of a dark roast coffee extract, the coffee extract was allowed to pass under the conditions of 25° C. and SV 8 [L/capacity [$m^3$]/flow rate [$m^3$/hr]].

The coffee extract treated above with the activated carbon was subjected to a pH adjustment with an aqueous solution containing sodium bicarbonate dissolved therein, and was then diluted with deionized water such that the content of chlorogenic acids was lowered to 170 mg/100 g.

The thus-obtained coffee composition was filled in a 190-g can, sealed, and subjected to retort sterilization processing at 121° C. for 12 minutes to produce a packaged black coffee beverage.

Example 4

Through a column (inner diameter: 45 mm, length: 150 mm) packed with activated carbon ("SHIRASAGI WH2C") in an amount as much as 50 wt % of the Brix degree of a medium roast coffee extract, the coffee extract was allowed to pass under the conditions of 25° C. and SV 8 [L/capacity [$m^3$]/flow rate [$m^3$/hr]].

The coffee extract treated above with the activated carbon was subjected to a pH adjustment with an aqueous solution containing sodium bicarbonate dissolved therein, and was then diluted with deionized water such that the content of chlorogenic acids was lowered to 170 mg/100 g.

The thus-obtained coffee composition was filled in a 190-g can, sealed, and subjected to retort sterilization processing at 131° C. for 100 seconds to produce a packaged black coffee beverage.

Example 5

Through a column (inner diameter: 45 mm, length: 150 mm) packed with activated carbon ("SHIRASAGI WH2C") in an amount as much as 50 wt % of the Brix degree of a medium roast and light roast, mixed coffee extract, the coffee extract was allowed to pass under the conditions of 25° C. and SV 8 [L/capacity [$m^3$]/flow rate [$m^3$/hr]].

The coffee extract treated above with the activated carbon was subjected to a pH adjustment with an aqueous solution containing sodium bicarbonate dissolved therein, and was then diluted with deionized water such that the content of chlorogenic acids was lowered to 350 mg/100 g.

The thus-obtained coffee composition was filled in a 190-g can, sealed, and subjected to retort sterilization processing at 131° C. for 100 seconds to produce a packaged black coffee beverage.

Comparative Example 2

Medium roast coffee beads were extracted with 8 volumes of deionized water (95° C.) to obtain a coffee extract. The coffee extract contained 0.00134 wt % of hydroxyhydroquinone before sterilization. By similar operations as in Example 1 except that no activated carbon treatment was performed, a pH adjustment was conducted and a packaged black coffee beverage was produced under the corresponding sterilization conditions shown in Table 1.

Results

As shown in Table 1, it has been found that the additional formation of hydroxyhydroquinone after heat sterilization can be inhibited by controlling the ratio of chlorogenic acids/solid content of coffee at 0.025 or higher. It is to be noted that the ratio of chlorogenic acids/solid content of coffee practically remains unchanged through heat sterilization.

Specific Example of Processing Before the Measurement of Chlorogenic Acids

Immediately after a packaged black coffee was opened, a portion (1 g) was accurately weighed. Its total volume was then increased to 10 mL with Eluent A (5 (V/V) % solution of acetonitrile containing 50 mM acetic acid, 10 mM sodium acetate and 0.1 mM 1-hydroxyethane-1,1-diphosphonic acid). Subsequent to filtration through a membrane filter ("GL CHROMATODISK 25A", pore size: 0.45 µm, GL Science, Inc.), the filtrate was provided for its analysis.

Specific Example of Processing Before the Measurement of Hydroxyhydroquinone Immediately after a packaged black coffee was opened, a portion (5 g) was accurately weighed. Its total volume was increased to 10 mL with a 5 (V/V) % methanol solution containing 0.5 (W/V) % phosphoric acid and 0.5 mM 1-hydroxyethane-1,1-diphosphonic acid. The solution was subjected to centrifugation to obtain a supernatant. The supernatant was allowed to pass through "BOND ELUTE JR SCX" (packed weight of solid phase: 500 mg, GL Science, Inc.), and an initial volume (approx. 1.0 mL) of passed solution was diverted to obtain the passed solution. The passed solution was subjected to filtration through a membrane filter ("GL CHROMATODISK 25A", pore size: 0.45 µm, GL Science, Inc.), and the filtrate was promptly provided for its analysis.

Specific Example of a Measurement of Hydrogen Peroxide

"SUPER ORITECTOR MODEL 5" (CENTRAL KAGAKU CORP.), a hydrogen oxide analyzer, was used. After it was calibrated with a standard calibration solution (hydrogen peroxide: 1 ppm), aliquots (1 mL) of 0.2 M phosphate buffer (pH 7.0) with 0.5% potassium bromate added therein were placed in measurement cells of the analyzer, respectively. At the time point that dissolved oxygen in the cell had been reduced to zero as a result of feeding of nitrogen, a commercial canned coffee and a test sample both of which had been allowed to stand in a 30° C. constant-temperature chamber were opened, and aliquots (1 mL) were promptly sampled and placed in the measurement cells, respectively. The measurement procedure of the analyzer was then followed to read the concentrations of produced oxygen from its printer. If extrapolation is needed, the oxygen concentrations are measured at every $15^{th}$ minute, the data up to 1 hour later are used to draw a straight line by the method of least squares, and then, the content of hydrogen peroxide is determined. The detection limit of "MODEL 5" was 0.1 mg/kg.

Referential Example 2

Evaluation of the hypotensive effects of the coffee composition Q prepared in Referential Example 1.

Experimental Materials and Procedure (a) After 13 to 14 weeks old, male spontaneously hypertensive rats (SHR) had been fully acclimatized to a blood pressure measurement procedure by provisionally measuring their blood pressures for 5 straight days with a commercial indirect blood-pressure meter for rats (manufactured by Softron Co., Ltd.), an evaluation test was performed. The rats were all reared under the conditions of 25±1° C., 55±10% R.H. and 12 hr lighting time (7:00 a.m. to 17:00 p.m.) (in rat-zone rearing rooms).

TABLE 1

|  |  | Ex. 1 | Ex. 2 | Ex. 3 | Ex. 4 | Ex. 5 | Comp. Ex. 1 | Comp. Ex. 2 |
|---|---|---|---|---|---|---|---|---|
| <Sterilization conditions> |  |  |  |  |  |  |  |  |
| Sterilization temperature | ° C. | 121 | 121 | 121 | 131 | 131 | 121 | 123 |
| Sterilization time | min | 12 | 12 | 12 | 1.67 | 1.67 | 12 | 10 |
| F0 value |  | 11.7 | 11.7 | 11.7 | 16.3 | 16.3 | 11.7 | 15.5 |
| Hydroxyhydroquinone before sterilization (analyzed by HPLC-electrochemical detector) | wt % | 0 | 0 | 0 | 0 | 0 | 0 | 0.00134 |
| <Analysis data after sterilization processing> |  |  |  |  |  |  |  |  |
| Chlorogenic acids (CGA) | wt % | 0.229 | 0.196 | 0.084 | 0.17 | 0.36 | 0.19 | 0.17 |
| Hydroxyhydroquinone (analyzed by HPLC-electrochemical detector) | wt % | 0.000032 | 0.000033 | 0.000044 | 0.000029 | 0.000032 | 0.00022 | 0.002 |
| Hydroxyhydroquinone/ chlorogenic acids × 100 | wt % | 0.0139 | 0.0168 | 0.0523 | 0.0164 | 0.0087 | 0.1158 | 1.15 |
| Chlorogenic acids/ solid content of coffee | wt. ratio | 0.1145 | 0.098 | 0.042 | 0.109 | 0.158 | 0.022 | 0.013 |
| 4-Caffeoylquinic acid/ 3-caffeoylquinic acid | wt. ratio | 0.96 | 0.96 | 0.97 | 0.83 | 0.87 | 0.72 | 0.89 |
| 5-Caffeoylquinic acid/ 3-caffeoylquinic acid | wt. ratio | 1.09 | 1.05 | 0.98 | 1.028 | 1.149 | 0.89 | 1.111 |
| $H_2O_2$ content |  | <DL* | <DL* | <DL* | <DL* | <DL* | <DL* | <DL* |
| pH |  | 5.4 | 5.4 | 5.4 | 5.9 | 5.8 | 5.4 | 6.1 |

DL: detection limit

Referential Example 1

A coffee beverage Q was produced by the following procedure.

Production of Coffee Treated with Activated Carbon

After a commercial instant coffee ("NESCAFE®, Gold Blend Red Label") (200 g) was dissolved in distilled water (1,400 mL) (the thus-prepared coffee will be called "a coffee composition P"), activated carbon "SHIRASAGI WH2C 28/42" (Japan EnviroChemicals, Ltd.) (30 g) was added. Subsequent to stirring for 1 hour, the mixture was filtered through a membrane filter (0.45 μm) to obtain a filtrate (this coffee will be called "a coffee composition Q"). The thus-obtained filtrate was lyophilized to afford a brown powder (15.8 g). That brown powder was dissolved in distilled water, and chlorogenic acids and hydroxyhydroquinone were quantitated by HPLC analysis. Chlorogenic acids and hydroxyhydroquinone were found to be contained at 4.12 wt % and lower than detection limit, respectively. Further, the content of potassium was also measured by ICP emission spectroscopy. The potassium content was found to be approx. 4.2 wt % in both the instant coffee as the raw material and the coffee treated with the activated carbon.

(b) Administration method and given dose: In the test group, the coffee composition Q (coffee treated with activated carbon) prepared in Referential Example 1 was used. In the control group, the commercial instant coffee was used. The coffee treated with the activated carbon and the instant coffee were separately dissolved in aliquots of physiological saline to prepare coffee beverages such that they would each give a dose of 200 mg/kg in terms of total chlorogenic acid dose. As their administration method, they were orally administered with feeding needles. The given dose was set at 5 mL/kg.

(c) Testing method: Four to six SHRs were used per group. The systolic blood pressure in the caudal vein was measured before the oral administration and also 12 hours after that, and the percentage blood pressure change after 12 hours was calculated from the blood pressure before the administration.

(d) Statistical processing method: From the measurement results so obtained, the means and standard deviations were calculated and a Student's t-tests was conducted. The significance level was set at 5%.

Results: As evident from Table 2, a pronounced hypotension was recognized from the ingestion of the coffee composition Q compared with the ingestion of the general instant coffee.

TABLE 2

|  | Control group | Test group |
|---|---|---|
| Administered coffee | Instant coffee | Coffee composition Q |
| # of cases | 4 | 6 |
| Percentage blood pressure change (%) (12 hours after administration) | −5.1 | −10.0* |
| Standard deviation | 1.0 | 0.6 |

*Had a significant difference from the control group at a percentage of risk not greater than 5%.

The invention claimed is:

1. A packaged black coffee liquid beverage comprising:
   (A) from 0.01 to 1 wt % of chlorogenic acids,
   (B) a weight ratio of hydroxyhydroquinone to chlorogenic acid of less than 0.1, and
   (C) a weight ratio of the chlorogenic acids to solid content of coffee of from 0.025 to 0.9
   wherein said packaged black coffee liquid beverage has been subjected to heat sterilization.

2. The packaged black coffee liquid beverage according to claim 1, wherein the weight ratio of the chlorogenic acids to solid content of coffee is from 0.04 to 0.2.

3. The packaged black coffee liquid beverage according to claim 2, wherein said chlorogenic acids comprise 3-caffeoylquinic acid, 4-caffeoylquinic acid and 5-caffeoylquinic acid in a weight ratio of 4-caffeoylquinic acid to 3-caffeoylquinic acid of from 0.6 to 1.2, and a weight ratio of 5-caffeoylquinic acid to 3-caffeoylquinic acid of from 0.01 to 3.

4. The packaged black coffee liquid beverage according to claim 2, wherein an oxygen permeability of a package is not higher than 5 [cc·mm/m$^2$·day·atm].

5. The packaged black coffee liquid beverage according to claim 1, wherein said chlorogenic acids comprise 3-caffeoylquinic acid, 4-caffeoylquinic acid and 5-caffeoylquinic acid in a weight ratio of 4-caffeoylquinic acid to 3-caffeoylquinic acid of from 0.6 to 1.2, and a weight ratio of 5-caffeoylquinic acid to 3-caffeoylquinic acid of from 0.01 to 3.

6. The packaged black coffee liquid beverage according to claim 1, wherein an oxygen permeability of a package is not higher than 5 [cc·mm/m$^2$·day·atm].

7. The packaged black coffee liquid beverage according to claim 1, wherein a weight ratio of hydroxyhydroquinone to chlorogenic acid is 0.001 to 0.07 wt %.

8. The packaged black coffee liquid beverage according to claim 1, wherein a weight ratio of hydroxyhydroquinone to chlorogenic acid is 0.002 to 0.05 wt %.

9. The packaged black coffee liquid beverage according to claim 1, wherein a weight ratio of hydroxyhydroquinone to chlorogenic acid is 0.003 to 0.03 wt %.

10. The packaged black coffee liquid beverage according to claim 1, wherein a weight ratio of hydroxyhydroquinone to chlorogenic acid is 0.004 to 0.02 wt %.

11. The packaged black coffee liquid beverage according to claim 1, wherein a weight ratio of hydroxyhydroquinone to chlorogenic acid is 0 wt %.

12. The packaged black coffee liquid beverage according to claim 1, wherein a chlorogenic acids/solid content of coffee weight ratio is 0.03 to 0.9.

13. The packaged black coffee liquid beverage according to claim 1, wherein a chlorogenic acids/solid content of coffee weight ratio is 0.04 to 0.8.

14. The packaged black coffee liquid beverage according to claim 1, wherein a chlorogenic acids/solid content of coffee weight ratio is 0.04 to 0.6.

15. The packaged black coffee liquid beverage according to claim 1, wherein a chlorogenic acids/solid content of coffee weight ratio is 0.04 to 0.4.

16. The packaged black coffee liquid beverage according to claim 1, wherein said packaged black coffee liquid beverage has a pH of from 5 to 7.

17. The packaged black coffee liquid beverage according to claim 1, wherein said packaged black coffee liquid beverage has a pH of from 5.4 to 6.5.

18. The packaged black coffee liquid beverage according to claim 1, wherein said packaged black coffee liquid beverage has a pH of from 5.6 to 6.3.

19. The packaged black coffee liquid beverage according to claim 1, wherein said packaged black coffee liquid beverage is packaged in at least one container selected from the group consisting of a PET bottle, an aluminum can, a steel can, a paper pack, a retort pouch and a glass bottle.

20. The packaged black coffee liquid beverage according to claim 1, wherein a content of chlorogenic acids is from 0.15 to 0.4 wt. %.

* * * * *